United States Patent
Cavalcanti Da Silva et al.

(10) Patent No.: US 11,866,761 B2
(45) Date of Patent: Jan. 9, 2024

(54) PROCESS FOR PRODUCING ESTERS AND BIOLUBRICANTS, CATALYSED BY FERMENTED SOLID

(71) Applicants: PETRÓLEO BRASILEIRO S. A.—PETROBRAS, Rio de Janeiro (BR); UNIVERSIDADE FEDERAL DO RIO DE JANEIRO—UFRJ, Rio de Janeiro (BR)

(72) Inventors: Jose Andre Cavalcanti Da Silva, Rio de Janeiro (BR); Guilherme Brandão Guerra, Rio de Janeiro (BR); Denise Maria Guimarães Freire, Rio de Janeiro (BR); Erika Cristina Gonçalves Aguieiras, Rio de Janeiro (BR); Elisa D'avila Cavalcanti Oliveira, Rio de Janeiro (BR); Jaqueline Greco Duarte, Rio de Janeiro (BR); Kassia Leone Ignacio, Rio de Janeiro (BR); Valéria Ferreira Soares, Rio de Janeiro (BR); Priscila Rufino Da Silva, Duque de Caxias (BR)

(73) Assignees: PETRÓLEO BRASILEIRO S.A.—PETROBRAS, Rio de Janeiro (BR); UNIVERSIDADE FEDERAL DO RIO DE JANEIRO—UFRJ, Rio de Janeiro (BR)

( * ) Notice: Subject to any disclaimer, the term of this patent is extended or adjusted under 35 U.S.C. 154(b) by 0 days.

(21) Appl. No.: 16/757,503

(22) PCT Filed: Oct. 11, 2018

(86) PCT No.: PCT/GB2018/052915
§ 371 (c)(1),
(2) Date: Apr. 20, 2020

(87) PCT Pub. No.: WO2019/077313
PCT Pub. Date: Apr. 25, 2019

(65) Prior Publication Data
US 2021/0189442 A1 Jun. 24, 2021

(30) Foreign Application Priority Data
Oct. 20, 2017 (BR) .................. 10 2017 022583-6

(51) Int. Cl.
*C12P 7/6458* (2022.01)
*C10M 105/38* (2006.01)
(Continued)

(52) U.S. Cl.
CPC ......... *C12P 7/6458* (2022.01); *C10M 105/38* (2013.01); *C10M 2207/2835* (2013.01);
(Continued)

(58) Field of Classification Search
CPC ....... C12P 7/649; C12P 7/6436; C12P 7/6458; C10M 105/38; C10M 2207/2835;
(Continued)

(56) References Cited

FOREIGN PATENT DOCUMENTS

| EP | 2657324 A1 * | 10/2013 | .......... C10M 105/38 |
| WO | 96/07751 A1 | 3/1996 | |
| WO | WO-9607751 A1 * | 3/1996 | .......... C10M 105/38 |

OTHER PUBLICATIONS

Aguieiras, E.C.G. et al., "Biodiesel production from Acrocomia aculeata acid oil by (enzyme/enzyme) hydroesterification process: Use of vegetable lipase and fermented solid as low-cost biocatalysts", OMICS Group; 2nd World Congress on Petrochemistry and Chemical Engineering, Oct. 27-29, 2014. (Year: 2014).*

(Continued)

*Primary Examiner* — Latosha Hines
(74) *Attorney, Agent, or Firm* — ARENTFOX SCHIFF LLP

(57) ABSTRACT

The present invention relates to a process for producing esters comprising reaction of methyl biodiesel or free fatty acids with a polyhydroxylated alcohol, in the presence of a biocatalyst, which is a fermented solid containing lipases of *Rhizomucor miehei* produced by culturing the microorganism on agricultural waste by solid state fermentation.

14 Claims, 4 Drawing Sheets

(51) Int. Cl.
    *C10N 60/00*     (2006.01)
    *C12R 1/645*     (2006.01)
    *C12N 1/14*     (2006.01)
    *C10N 70/00*     (2006.01)

(52) U.S. Cl.
    CPC ...... *C10N 2060/01* (2020.05); *C10N 2070/00* (2013.01); *C12N 1/145* (2021.05); *C12R 2001/645* (2021.05)

(58) Field of Classification Search
    CPC ......... C10M 2207/283; C10N 2060/01; C10N 2070/00; C10N 2020/02; C10N 2030/02; C10N 2030/06; C10N 2030/10; C12R 2001/645; C12N 1/145
    See application file for complete search history.

(56) References Cited

OTHER PUBLICATIONS

International Search Report and Written Opinion corresponding to PCT/GB2018/052915 dated Apr. 11, 2019.

Cavalcanti Da Silva, J.A. et al., "Enzymatic production and characterization of potential biolubricants from castor bean biodiesel", Journal of Molecular Catalysis B: Enzymatic, vol. 122, Oct. 14, 2015 (Oct. 14, 2015), p. 323-329, XP029314725.

Monot, F. et al., "Enzymatic Synthesis of Neopentylpolyol Esters in Organic Media", Applied Biochemistry and Biotechnology, Part A: Enzyme Engineering and Biotechnology, vol. 24-25, No. 1, Mar. 1990 (Mar. 1990), p. 375-386, XP035176606.

Aguieiras, E.C.G. et al., "Biodiesel production from Acrocomia aculeata acid oil by (enzyme/enzyme) hydroesterification process: Use of vegetable lipase and fermented solid as low-cost biocatalysts", OMICS Group; 2nd World Congress on Petrochemistry and Chemical Engineering, Oct. 27-29, 2014, Las Vegas, USA. XP002788490.

\* cited by examiner

PROCESS FOR PRODUCING ESTERS AND BIOLUBRICANTS, CATALYSED BY FERMENTED SOLID

CROSS-REFERENCE TO RELATED APPLICATION

This application is a U.S. National Stage entry under 35 U.S.C. § 371 based on International Application PCT/GB2018/052915, filed on Oct. 11, 2018, which claims the benefit of priority to BR 10 2017 022583-6, filed Oct. 20, 2017 which is incorporated herein by reference in its entirety.

FIELD OF THE INVENTION

The present invention relates to the field of biocatalysis. More specifically, the present invention relates to the development of new biocatalytic routes that extend the possibilities for obtaining, by the enzymatic route, esters that can be used as biolubricants.

BACKGROUND OF THE INVENTION

Basic oils are the main constituents of lubricating oils and may be classified as mineral (obtained by distillation and refining of petroleum) and synthetic (obtained on the basis of chemical reactions of materials from the petrochemical industry). Although only a small fraction of the consumption of petroleum is in the production of lubricants, a high percentage of these products are not discarded properly, thus representing a threat to the environment. By way of illustration, it is important to bear in mind that leakage of one litre of mineral lubricant can contaminate $1 \times 10^6$ litres of water.

The increasingly stringent requirements imposed by environmental legislation, such as European standard EN13432, the demand for food-grade lubricants for the industries in that field in certain countries and questions regarding the limited availability of fossil resources have contributed to the development of products derived from alternative sources, and constitutes one of the main priorities in the oil-chemical sector.

Biolubricants are biodegradable lubricants that can be broken down by microbial action, are generally obtained from vegetable oils modified by chemical reactions and are used in applications where the possibility of leaks may compromise the environment.

In general, biodegradability denotes the tendency of a lubricant to be metabolized by microorganisms in up to a year. The form in which the microorganisms cause decomposition depends essentially on their structures. Vegetable oils are typically 99% biodegradable, usually falling to 90% to 98% after mixing with additives.

The main types of esters used as biolubricants are diesters, phthalates, trimellitates, C36 dimerates and polyol esters. The polyol esters are produced in reactions between polyhydric alcohols and mono- or dicarboxylic acids. This class of product offers extraordinary stability owing to the absence of a secondary hydrogen in the β position and the presence of a central quaternary carbon atom.

The reaction employed in the production of esters useful as biolubricants catalysed by chemical catalysts is known in the prior art.

Document BR 10 2013 033582 7 describes the production of biolubricants on the basis of transesterification reactions of biodiesel from castor oil with trimethylolpropane alcohol catalysed by dibutyltin dilaurate (DBTDL). It should be noted that the reaction conditions when using DBTDL are harsh, requiring temperatures between 168° C. and 172° C. and vacuum.

Enzymatic catalysts, or biocatalysts, offer various advantages compared to chemical catalysts. These advantages include high selectivity of the enzymes for their substrates, high yields, milder reaction conditions, such as temperature and pressure, no degradation of equipment, and biodegradability of the biocatalyst, for example.

However, the high cost of the commercially available enzyme preparations has been an obstacle to the economic viability of their industrial application in the synthesis of products of lower added value and high sales volume.

The use of enzymes in the form of fermented solids, produced by solid state fermentation, represents an alternative for reducing the costs of production, since steps of extraction and purification of the enzyme are eliminated.

Patent document PI0704791-6 relates to a process for synthesis of esters, for use as biodiesel, which employs reactions catalysed by lipases in the form of fermented solid, produced by solid state fermentation, by the bacterium *Burkholderia cepacia*.

In the process in said document of the prior art, fatty acids (in the case of esterification reactions) or a source of triglycerides (in the case of transesterification reactions) are reacted with a monohydroxylated alcohol, which is preferably ethanol. The document, apart from using an enzyme of bacterial origin, does not envisage transesterification and hydroesterification reactions employing a polyhydroxylated alcohol.

It can be inferred that, to date, a process has not been described in the prior art for obtaining biolubricant esters that uses transesterification and hydroesterification reactions employing a polyhydroxylated alcohol, catalysed by fermented solids obtained by culture of microorganisms on agricultural waste.

The present invention, involving the use of low-cost lipases, contributes to the economic feasibility of the production of biolubricants by the enzymatic route, as well as utilization of biomass.

SUMMARY OF THE INVENTION

The aim of the present invention is to provide a process for producing esters that solves the main problems of the prior art enumerated above.

In order to achieve this aim, the present invention provides a process for producing esters that involves the reaction of methyl biodiesel or free fatty acids (FFAs) with a polyhydroxylated alcohol in the presence of a biocatalyst, wherein the biocatalyst is a fermented solid produced by culture of a microorganism in agricultural waste, by solid state fermentation.

Another aim of the present invention relates to the use of the esters produced as biolubricants.

Another aim of the present invention relates to the biolubricants comprising the esters produced by the process of the present invention.

DETAILED DESCRIPTION OF THE INVENTION

Unless they are defined otherwise, all the technical and scientific terms used here have the same meaning as understood by a person versed in the subject matter to which the invention relates. The terminology used in the description of the invention has the sole purpose of describing particular embodiments, and is not intended to limit the scope of the teaching. Unless stated otherwise, all the numbers expressing quantities, percentages and proportions, and other numerical values used in the specification and in the claims, must be understood as being qualified, in all cases, by the term "about". Thus, unless stated otherwise, the numerical parameters shown in the specification and in the claims are approximations that may vary, depending on the properties to be obtained.

The present inventors solved the problem of the prior art by providing a process for producing esters that comprises reacting methyl biodiesel or free fatty acids with a polyhydroxylated alcohol, in the presence of a biocatalyst, wherein the biocatalyst is a fermented solid, produced by culturing a microorganism in agricultural waste by solid state fermentation.

In a first aspect, the present invention involves the production of low-cost lipases for use in the synthesis of biolubricant esters. For this purpose, agricultural wastes are used as the culture medium in the solid state fermentation process.

Solid state fermentation makes it possible to use low-cost raw materials as the culture medium for microorganisms, having a single fermentation medium. In this process, the substrates not only supply nutrients for culture of the microorganisms, but also serve as support for growth of the cells.

In the context of the present invention, the term "agricultural waste(s)" is to be understood as solid residues (cakes) of oleaginous raw materials. Preferably, solid residues from the extraction of palm oil and cottonseed oil are used.

The term "inoculum" is to be understood as cells of microorganisms, in the form of spores or vegetative cells, used for initiating the fermentation process. Preferably, the microorganism is a filamentous fungus. More preferably, the fungus is of the genus *Rhizomucor*. Even more preferably, the fungus is of the species *Rhizomucor miehei*.

The term "fermenter" is to be understood as a chamber with controlled temperature and humidity for development of the microorganism on the cakes.

The term "fermented solid" is to be understood as the dry fermented cake at the end of the solid state fermentation process containing the biomass of the microorganism and lipases.

In one embodiment, water is added to the palm oil cake or cottonseed oil cake, the substrate for solid state fermentation, in the proportion ideal for the fermentation process, and then the inoculum is mixed in.

The moistened and inoculated cake is then incubated in the fermenter, during which the microorganism grows and, as a result of its metabolism, produces a set of lipases with high synthesis capacity.

At the end of solid state fermentation, the fermented cake is submitted to a drying step before being used in catalysis of the reactions. Preferably, drying is carried out by lyophilization or by forced aeration.

The low-cost enzymatic biocatalyst produced by the solid state fermentation process is used in transesterification or hydroesterification reactions for production of the biolubricant esters.

In the transesterification process, methyl biodiesels are reacted with polyhydroxylated alcohols, producing the biolubricant esters. Preferably, the methyl biodiesel is soya methyl biodiesel or castor oil methyl biodiesel. Preferably, the polyhydroxylated alcohol is neopentyl glycol, trimethylolpropane or pentaerythritol.

In one embodiment, the transesterification reaction is carried out in the biodiesel:alcohol molar ratio from 2 to 5 and optionally 1 to 3% (w/w) of water. The fermented solid is used as a biocatalyst in a concentration from 10 to 30% (w/w). The reaction is carried out in the reactor, with stirring, at a temperature from 30 to 50° C., at atmospheric pressure.

In a preferred embodiment, the reactor used is a controlled-temperature stirred tank at atmospheric pressure, in which the transesterification reaction takes place.

In these conditions, methyl esters are transesterified with the alcohol, producing the biolubricant esters and methanol as a by-product. Said product is separated at the end of the process.

The hydroesterification process consists of a first hydrolysis reaction and a second reaction of esterification.

In one embodiment, the first reaction (hydrolysis) comprises mixing an oleaginous oil and a buffer, in a ratio of 1:1 volume/volume, followed by addition of a lipase in a proportion from 1 to 2% w/v of the weight of oil.

The reaction is carried out in the reactor with stirring, at a temperature from 30 to 40° C., at atmospheric pressure. In these conditions, the oil is hydrolysed and the free fatty acids and glycerol are produced as by-products. The free fatty acids are separated from the buffer, from the glycerol and from the lipase before being used in the esterification reaction.

In a preferred embodiment, the oleaginous oil is soya oil or castor oil and the lipase is a commercial lipase from *Candida rugosa* or lipases obtained from dormant castor oil plant seeds.

In a preferred embodiment, the reactor used is a controlled-temperature stirred tank at atmospheric pressure, in which the hydrolysis reaction takes place.

In one embodiment, the second reaction (esterification) is carried out by mixing free fatty acids and a polyhydroxylated polyol alcohol, in the molar ratio of free fatty acids to alcohol from 2 to 5 and optionally 1 to 3% (w/w) of water.

The fermented solid is used as a biocatalyst in a concentration from 10 to 30% (w/w). The reaction is carried out in the reactor with stirring, at a temperature from 30 to 50° C., at atmospheric pressure.

In a preferred embodiment, the reactor used is a controlled-temperature stirred tank at atmospheric pressure, in which the esterification reaction takes place.

In these conditions, the free fatty acids are esterified with the polyol, producing the biolubricant esters and water as by-product.

The biolubricant esters obtained by the process of the present invention were analysed with respect to their physicochemical properties, displaying satisfactory physicochemical characteristics in line with the biolubricants currently available.

The viscosity of the biolubricants is the most important property of these fluids, as it is directly related to the formation of the film that will protect metallic surfaces against attack.

The viscosity index is a parameter for the behaviour of the viscosity of oils at temperature. The higher the value, the smaller are the changes in viscosity of the oil with temperature changes. Normally, the value of the viscosity index is determined by calculations that take into account the viscosity of the product at 40° C. and at 100° C.

The flow point measures the minimum temperature at which the oil still flows and is a test used for assessing the behaviour of lubricating oils when subjected to low temperatures.

The physicochemical properties such as viscosity, viscosity index and flow point of biolubricants are higher compared to the mineral-base lubricants.

The properties and performance of the biolubricants of the present invention may be further improved by using additives that are compatible with the lubricants, and preferably that are non-toxic and biodegradable.

The esters produced by the process of the present invention are especially useful in lubrication applications in which the maximum operating temperatures are below 120° C., but in which the ambient temperature remains above −40° C.

The biolubricants of the present invention may be used as motor oil, hydraulic fluid, rolling fluid, etc.

The present invention will be further illustrated by the following examples, which are not to be regarded as limiting. As will be obvious to a person skilled in the art, the invention is not limited to these particular embodiments.

EXAMPLES

Example 1—Production of the Fermented Solid

The fermented solid of *Rhizomucor miehei* was obtained as a result of fermentation of cottonseed oil cake (crushed) or palm oil cake (crushed and sieved—particles smaller than 1.18 mm). The fermentations were carried out in beakers containing 15 g of cake with water content adjusted to 65 and 50%, for the palm oil cake and cottonseed oil cake, respectively. Each beaker containing the cake was sterilized at 121° C. for 15 minutes in an autoclave and the cake was inoculated with $10^7$ spores of *R. miehei* per gram of solid (dry weight) and incubated at 30° C. in a climate chamber with relative moisture of 90%, for 72 h. At the end of fermentation, the fermented medium was lyophilized and stored at 4° C. until used. Fermented solids of *R. miehei* were obtained by solid state fermentation using palm oil cake or cottonseed oil cake as raw materials, with hydrolytic activity of 17±2 U/g and 29±1 U/g, respectively.

Example 2—Hydrolytic Activity

The hydrolytic activity of the fermented solid was estimated from the change in absorbance in spectrophotometry promoted by hydrolysis of the substrate p-nitrophenyl laurate (p-NFL) at a concentration of 25 mM in solution of acetonitrile/dimethyl sulphoxide (DMSO) 1:1. For the reaction of hydrolysis of the substrate, an aliquot of 250 μL of the solution of p-NFL was diluted in 2.2 mL of sodium phosphate buffer pH 7.0 (25 mM) in the cell, which was acclimatized at 30° C. for 2 minutes. After this time, an aliquot of 50 μL of the liquid enzymatic extract was added, and the absorbance was monitored in the spectrophotometer (SHIMADZU UV-1800) at 412 nm. One enzyme unit (U) corresponds to the amount of enzyme capable of producing 1 μmol of p-nitrophenol per minute, in the test conditions. The activity is calculated using Equation 1:

$$\text{Activity (U/mL)} = \frac{\alpha \times D \times f \times V_f}{V_s} \quad \text{(Equation 1)}$$

where:
α=change in absorbance (ΔAbs) in the time interval Δt (in minutes) elapsed during the phase of linear increase in absorbance;
D=dilution of the enzyme solution;
f=conversion factor (0.094 μmol·L$^{-1}$), obtained by constructing a standard curve of p-NFL at a concentration varying between 0.01 and 0.2 μmol·mL$^{-1}$;
Vf=reaction volume, which is the volume of the solution of p-NFL in the buffer and the volume of the sample (mL);
Vs=volume of the enzyme solution used in the test (mL).

The hydrolytic activity expressed per gram of dry cake (U/g) was calculated from Equation 2:

$$\text{Activity (U/g)} = \frac{(\text{U/mL}) \times V_t}{m} \quad \text{(Equation 2)}$$

where:
Vt=volume of buffer used in extraction of the enzyme;
m=dry weight of cake.

Example 3—Transesterification Reaction

Example 3.1—Soya Biodiesel and Neopentyl Glycol Alcohol

The reaction between soya biodiesel and neopentyl glycol alcohol resulted in a product with conversion of 85.5% after 48 h of reaction catalysed by the fermented solid of *R. miehei* produced on palm oil cake.

Figure 1:
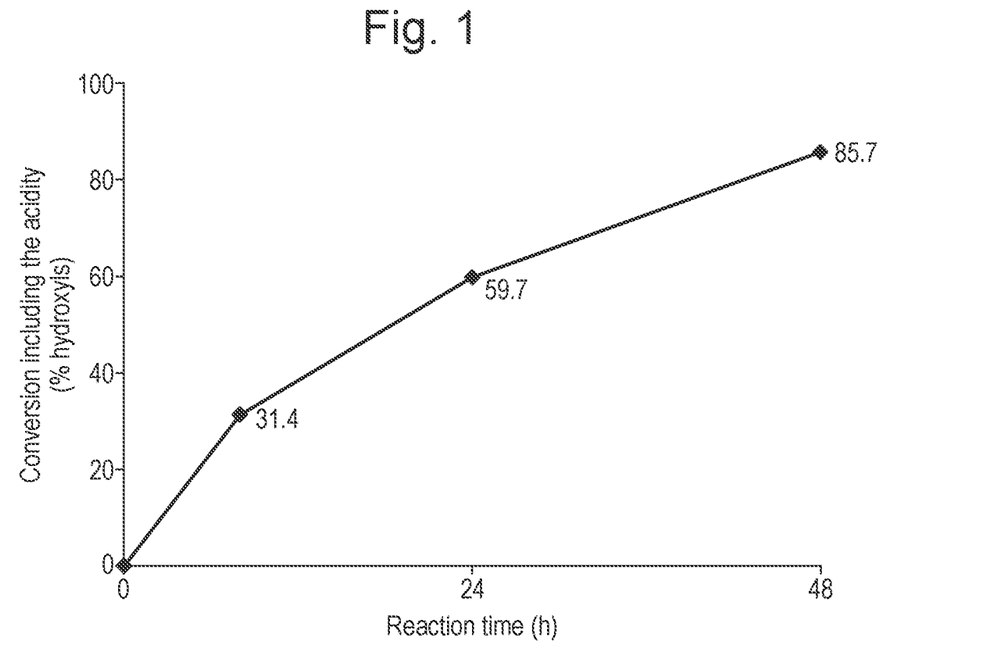
FIG. 1 shows the synthesis of biolubricants based on the reaction between soya biodiesel and neopentyl glycol alcohol catalysed by the lipases of *R. miehei* present in the fermented solid of palm oil cake.

The reaction of soya biodiesel with neopentyl glycol alcohol took place in the molar ratio from 2:1 to 3.1:1 alcohol/biodiesel, 10 to 30% (w/w) of biocatalyst, with water content from 1 to 2.5% (w/w) and temperature from 35 to 50° C. with stirring at atmospheric pressure (FIG. 1).

The product of the reaction between soya biodiesel and neopentyl glycol alcohol catalysed by the lipases of the fermented solid of palm oil cake was produced in considerable volume (200 ml) and was characterized, to determine the properties of the biolubricant produced (Table 1). With the exception of the acidity index, all the other properties assessed were satisfactory.

TABLE 1

Characteristics of the biolubricant produced in the reaction between soya biodiesel and neopentyl glycol alcohol.

| Test | Result |
| --- | --- |
| Moisture (ppm) | 884.4 |
| Viscosity 100° C. (mm$^2$/s) | 4.290 |
| Viscosity 40° C. (mm$^2$/s) | 15.41 |
| Viscosity index | 206 |
| Fluidity (° C.) | −6 |
| Acidity index (mgKOH/g) | 19.8 |
| Rotary pump (min) | 30 |

Figure 2:
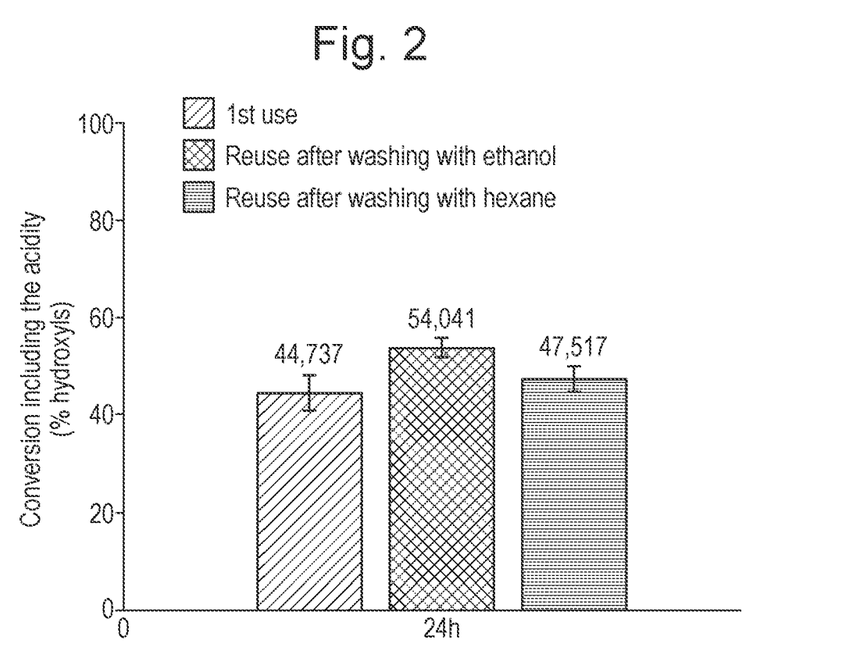
FIG. 2 shows the reuse of the fermented solid of palm oil cake in the synthesis of biolubricant based on the reaction between soya biodiesel and neopentyl glycol alcohol.
Figure 7:
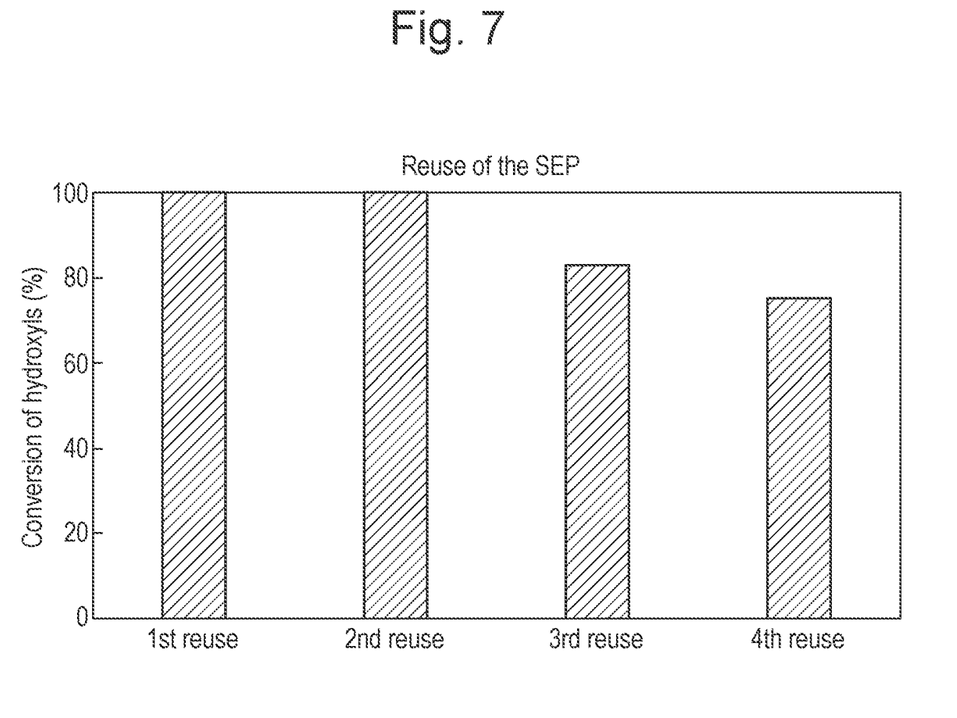
FIG. 7 shows the activity of the fermented solid (SEP) of palm oil cake, after reuse several times, without washing with solvent, in the synthesis of biolubricants.

The fermented solid of palm oil cake was assessed with respect to reuse in reactions between soya biodiesel and neopentyl glycol. After a reaction time of 24 h or 72h, the enzyme was washed with solvent (hexane or ethanol) followed by filtration in a Buchner funnel and incubation overnight in a desiccator. At the end of this procedure, the enzyme was used again in the reaction as described in example 1. The fermented solid of palm oil cake can be reused at least once after washing with hexane or ethanol (FIG. 2). Reuse without washing with solvent was also tested. In this case, the product, after reaction for 72 h, was removed at the top of the reactor after decanting the fermented solid. Then fresh reaction medium was added to the reactor, equivalent in weight to the weight of product withdrawn (FIG. 7).

Example 3.2—Castor Oil Biodiesel and Alcohols Trimethylolpropane and Pentaerythritol Reaction between castor oil biodiesel and the alcohols trimethylolpropane and pentaerythritol resulted in a product with conversion of 52% in 72 h, respectively. The reactions were carried out with fermented solid of R. miehei produced on palm oil cake as biocatalyst.

Figure 3:
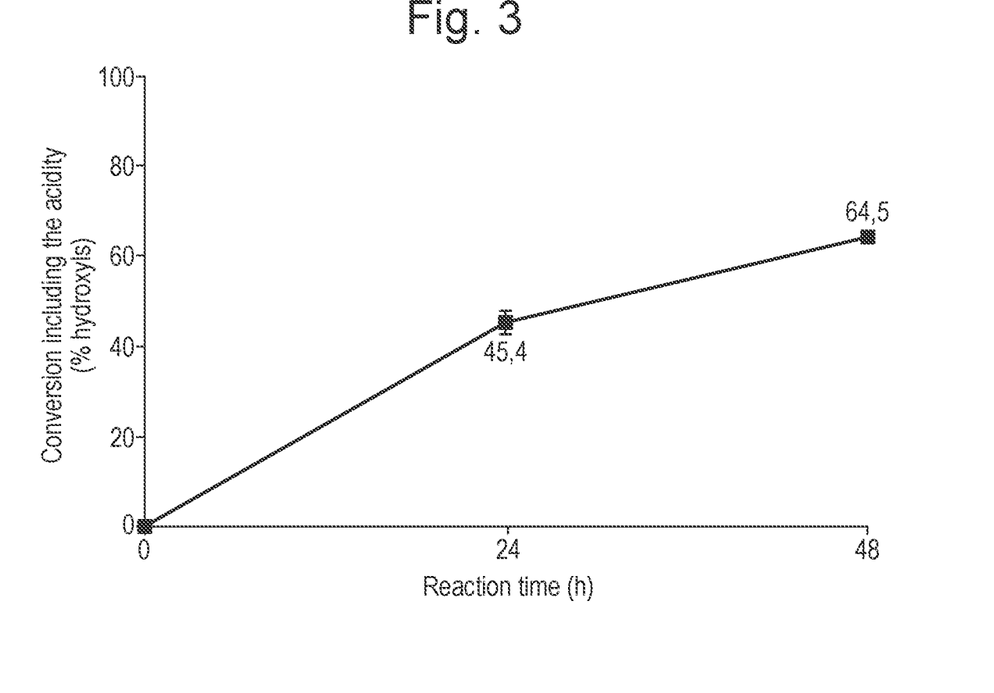
FIG. 3 shows the synthesis of biolubricant based on the reaction between castor oil biodiesel and trimethylolpropane alcohol catalysed by the lipases of *R. miehei* present in the fermented solid of palm oil cake.

Reaction of castor oil biodiesel with the alcohols trimethylolpropane and pentaerythritol took place in the molar ratio from 2 to 3.75:1 alcohol/biodiesel, 10 to 30% (w/w) of biocatalyst, with water content from 1 to 3% (w/w) and temperature from 30 to 50° C. with stirring at atmospheric pressure (FIG. 3).

Example 3.3—Castor Oil Biodiesel and Neopentyl Glycol Alcohol

Reaction between castor oil biodiesel and neopentyl glycol alcohol resulted in a product with conversion of 91% in 96 h. The reactions were carried out with fermented solid of R. miehei produced on cottonseed oil cake as biocatalyst.

Figure 4:
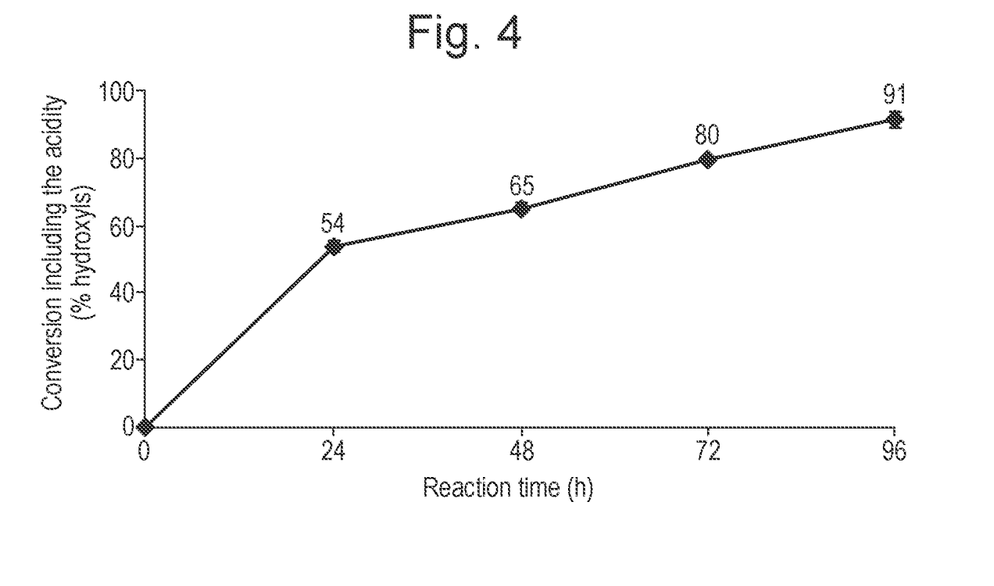
FIG. 4 shows the synthesis of biolubricant based on the reaction between castor oil biodiesel and neopentyl glycol alcohol catalysed by the lipases of *R. miehei* present in the fermented solid of cottonseed oil cake.

Reaction of castor oil biodiesel with neopentyl glycol alcohol took place in the molar ratio from 2 to 4:1 alcohol/biodiesel, 10 to 30% (w/w) of biocatalyst, with water content from 1 to 3% (w/w) and temperature from 30 to 50° C. with stirring at atmospheric pressure (FIG. 4).

The product of the reaction between castor oil biodiesel and neopentyl glycol alcohol catalysed by the lipases of the fermented solid of palm oil cake was produced in considerable volume (200 ml) and was characterized, to determine the properties of the biolubricant produced (Table 2). With the exception of the acidity index, the other properties were satisfactory.

TABLE 2

Characteristics of the biolubricant produced in the reaction between castor oil biodiesel and neopentyl glycol alcohol.

| Test | Result |
| --- | --- |
| Moisture (ppm) | 541.9 |
| Viscosity 100° C. (mm$^2$/s) | 86.57 |
| Viscosity 40° C. (mm$^2$/s) | 8.854 |
| Viscosity index | 66 |
| Fluidity (° C.) | −39 |
| Acidity index (mgKOH/g) | 87.5 |
| Rotary pump (min) | 29 |
| Rancimat (h) | 6.5 |

The fermented solid of cottonseed oil cake was assessed with respect to reuse in the reactions between castor oil biodiesel and neopentyl glycol. After a reaction time of 24 h, the enzyme was washed with solvent (ethyl ether or ethanol) followed by filtration in a Buchner funnel and incubation overnight in a desiccator. At the end of this procedure, the enzyme was used again in the reaction as described above. The cotton SEP can be reused at least once after washing with ether or ethanol.

Example 4—Reactions of Hydroesterification

Example 4.1—Free Fatty Acids (FFAs) of Castor Oil and Neopentyl Glycol Alcohol

Reaction between FFAs of castor oil and neopentyl glycol alcohol resulted in a product with conversion of 65% in 96 h. The reactions were carried out with fermented solid of R. miehei produced on cottonseed oil cake as biocatalyst.

Figure 5:
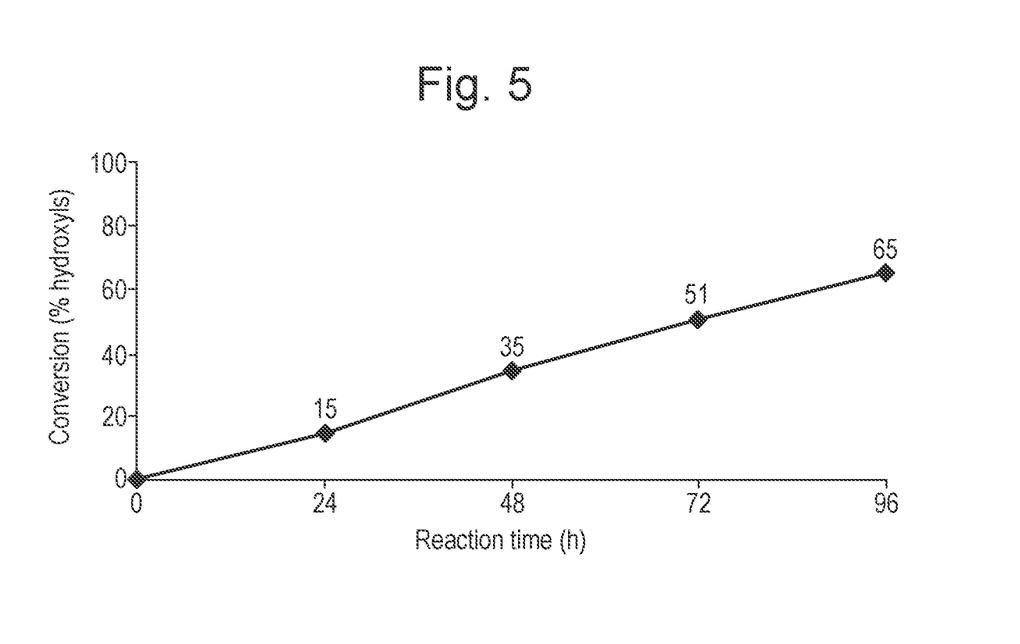
FIG. 5 shows the synthesis of biolubricant based on the reaction between the free fatty acids of castor oil and neopentyl glycol alcohol catalysed by the lipases of *R. miehei* present in the fermented solid of cottonseed oil cake.

Reaction of FFAs of castor oil with neopentyl glycol alcohol took place in the molar ratio from 2 to 4:1 alcohol/FFAs, 10 to 30% (w/w) of biocatalyst, with water content from 1 to 3% (w/w) and temperature from 30 to 50° C. with stirring at atmospheric pressure (FIG. 5).

The product of the reaction between the FFAs of castor oil and neopentyl glycol alcohol catalysed by the lipases of the cotton SEP was produced in considerable volume (200 ml) and was characterized, to determine the properties of the biolubricant produced (Table 3). With the exception of the acidity index, all the other properties assessed were satisfactory.

TABLE 3

Characteristics of the biolubricant produced in the reaction between FFAs of castor oil and neopentyl glycol alcohol.

| Test | Result |
| --- | --- |
| Moisture (ppm) | 873.5 |
| Viscosity 100° C. (mm$^2$/s) | 152.2 |
| Viscosity 40° C. (mm$^2$/s) | 13.04 |
| Viscosity index | 73 |
| Fluidity (° C.) | −33 |
| Acidity index (mgKOH/g) | 100.4 |
| Rotary pump (min) | 42 |
| Rancimat (h) | 114.5 |

Example 4.2—Soya Free Fatty Acids (FFAs) and Neopentyl Glycol Alcohol

Reaction between the soya FFAs and neopentyl glycol alcohol resulted in a product with conversion of 82% in 72 h. The reactions were carried out with fermented solid of R. miehei produced on cottonseed oil cake as biocatalyst.

Figure 6:
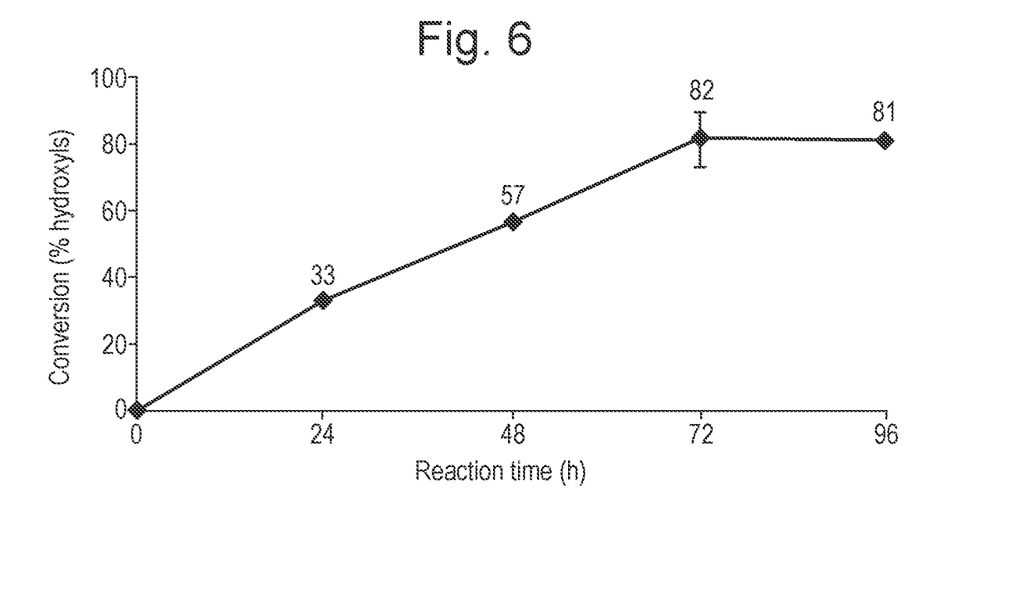
FIG. 6 shows the synthesis of biolubricant based on the reaction between the free fatty acids of soya and neopentyl glycol alcohol catalysed by the lipases of *R. miehei* present in the fermented solid of cottonseed oil cake.

Reaction of soya FFAs with neopentyl glycol alcohol took place in the molar ratio from 2 to 4:1 alcohol/FFAs, 10 to 30% (w/w) of biocatalyst, with water content from 1 to 3% (w/w) and temperature from 30 to 50° C. with stirring at atmospheric pressure (FIG. 6).

The product of the reaction between the soya FFAs and neopentyl glycol alcohol catalysed by the lipases of the cotton SEP was produced in considerable volume (200 mL) and was characterized, to determine the properties of the biolubricant produced (Table 4). With the exception of the acidity index, fluidity and moisture, all the other properties assessed were satisfactory.

TABLE 4

Characteristics of the biolubricant produced in the reaction between Soya FFAs and neopentyl glycol alcohol.

| Test | Result |
|---|---|
| Moisture (ppm) | 2150.3 |
| Viscosity 100° C. (mm²/s) | 20.27 |
| Viscosity 40° C. (mm²/s) | 5.034 |
| Viscosity index | 191 |
| Fluidity (° C.) | 15 |
| Acidity index (mgKOH/g) | 105.5 |
| Rotary pump (min) | 28 |
| Rancimat (h) | 3.08 |

Example 5—Determination of the Acidity of the Reactions

The content of free fatty acids in the oils and products was determined by neutralization titrimetry. The free fatty acids, about 0.2 g of the sample, were titrated with 0.04 mol·L$^{-1}$ NaOH solution in a Mettler model DG20 automatic titrator up to a pH of 11.0 and the acidity of the sample was determined from Equation 3.

Alternatively, for samples with a larger volume, the free fatty acids, from about 0.5 to 1 g of the sample, were titrated with 0.25 mol·L$^{-1}$ NaOH solution using phenolphthalein as indicator and the acidity of the sample was determined from Equation 3.

$$\text{Acidity (\% w/w)} = \frac{V \times M \times AG}{10 \times m} \quad \text{(Equation 3)}$$

where:
V=volume of sodium hydroxide used in titration of the sample (mL);
M=molarity of the NaOH solution (mol·L$^{-1}$);
AG=molecular weight of the fatty acid present in highest concentration in the oil* (g);
m=sample weight (g).
*Soya oil=linoleic acid (280 g); castor oil=ricinoleic acid (298 g).

Example 6—Determination of the Content of Methyl Esters

To determine the content of the methyl ester (biodiesel) in the products of the transesterification reactions, 20 μL aliquots were diluted in 480 μL of n-heptane and injected in the chromatograph. A gas chromatograph was used (SHIMADZU 2010), equipped with a flame ionization detector (FID) and omegawax capillary column (length of 30 m, inside diameter 0.25 mm and film thickness 0.25 μm). The conditions of the analyses were: initial temperature of 200° C. for 5 minutes, and then programmed at a rate of 20° C./min up to 260° C., remaining at 260° C. for 6 min. The temperatures of the detector and of the injector were 250° C. and 260° C., respectively. Helium was used as the carrier gas, at a flow rate of 2.0 mL/min and injection was done in split mode of 1:20. Methyl heptadecanoate was used as the internal standard and the content of esters was calculated using Equation 4.

$$\text{Content of ester (\% w/w)} = \frac{weight_{standard} \times area_{ester} \times 100}{area_{standard} \times weight_{sample}}$$

Example 7—Conversion in the Esterification Reactions

The conversion of free fatty acids to biolubricants was monitored by the titrimetric method (acidity), in which the consumption of the FFAs was observed. The conversion of the reaction was calculated from Equation 5 or Equation 6.

The results from Equation 5 are expressed in the form of percentage of FFA esterified disregarding the excess of FFA in the reactions, so that 100% conversion is equivalent to 100% of the hydroxyls of the alcohol being esterified. The results from Equation 6 are expressed in the form of percentage of FFA esterified, so that 100% conversion is equivalent to 100% of the FFAs esterified.

$$\text{Conversion (\% hydroxyls)} = \frac{100 \times (A_i - A_f) \times RM}{H \times A_i} \quad \text{(Equation 5)}$$

$$\text{Conversion (\% FFA)} = \frac{100 \times (A_i - A_f)}{A_i} \quad \text{(Equation 6)}$$

where:
$A_i$=initial acidity (% w/w);
$A_f$=final acidity (% w/w);
RM=initial molar ratio FFA/alcohol;
H=number of hydroxyls in the alcohol molecule

Example 8—Conversion in the Transesterification Reaction

The conversion in the transesterification reaction was calculated from Equation 7. The results are expressed in the form of percentage of biodiesel transesterified, disregarding the excess of biodiesel in the reactions and the free fatty acids formed, so that 100% conversion is equivalent to 100% of the hydroxyls of the alcohol being esterified.

$$\text{Conversion including acidity (\% hydroxyls)} = \quad \text{(Equation 7)}$$
$$\frac{100 \times (E_i - (E_f + (A_f - A_i))) \times RM}{H \times E_i}$$

where:
Ei=initial ester content (% w/w);
Ef=final ester content (% w/w);
Ai=initial acidity (% w/w);
Af=final acidity (% w/w);
RM=initial molar ratio biodiesel/alcohol;
H=number of hydroxyls in the alcohol molecule It will be obvious that the above examples have only been presented for purposes of illustration, and that changes and variations thereof, obvious to a person skilled in the art, are considered to be included in the scope of the present invention, as defined in the claims given hereunder.

The invention claimed is:

1. A process for producing biolubricant esters, comprising:
   a) culturing a microorganism on agricultural waste by solid state fermentation to obtain a biocatalyst; and
   b) reacting methyl biodiesel or free fatty acids with a polyhydroxylated alcohol in the presence of the biocatalyst obtained from step a) to generate one or more biolubricant esters,
   wherein
   the agricultural waste is cottonseed cake or palm oil cake;
   the biocatalyst comprises a fermented solid produced by the solid state fermentation of the agricultural waste by the microorganism; and
   the methyl biodiesel is soya biodiesel or castor oil biodiesel.

2. The process according to claim 1, wherein the reaction of the methyl biodiesel with the polyhydroxylated alcohol in step c) is a transesterification reaction.

3. The process according to claim 1, wherein the reaction of the free fatty acids with the polyhydroxylated alcohol in step c) is a hydroesterification reaction.

4. The process according to claim 1, wherein the biocatalyst is used at a concentration from 10 to 30 percentage by weight (wt %).

5. The process according claim 1, wherein a molar ratio from 2:1 to 5:1 of the polyhydroxylated alcohol to the methyl biodiesel or the free fatty acids is used.

6. The process according to claim 1, wherein the free fatty acids are obtained by reaction of soya oil or castor oil with a biocatalyst.

7. The process according to claim 6, wherein the biocatalyst comprises a plurality of lipases.

8. The process according to claim 1, wherein the polyhydroxylated alcohol is neopentyl glycol, trimethylolpropane or pentaerythritol.

9. The process according to claim 1, wherein the microorganism is a fungus.

10. The process according to claim 9, wherein the fungus is *Rhizomucor miehei*.

11. The process according to claim 1, wherein
    the one or more esters are generated in step c) by adding the biocatalyst, in the form of a lyophilizate, to a mixture comprising the methyl biodiesel or free fatty acids and the polyhydroxylated alcohol.

12. The process according to claim 1, wherein the fermented solid is reused at least once.

13. The process according to claim 1, wherein the process further comprises:
    d) purifying the one or more esters produced by reacting the methyl biodiesel or the free fatty acids with the polyhydroxylated alcohol.

14. The process according to claim 1, wherein the agricultural waste is palm oil cake.

* * * * *